United States Patent
Iyer et al.

(10) Patent No.: US 6,248,309 B1
(45) Date of Patent: Jun. 19, 2001

(54) GUMS CONTAINING ANTIMICROBIAL AGENTS

(75) Inventors: Lokanathan M. Iyer, Bellevue; Dawn E. Barkans, Redmond; Brian D. Hench, Shoreline, all of WA (US)

(73) Assignee: Optiva Corporation, Snoqualmie, WA (US)

( * ) Notice: Subject to any disclaimer, the term of this patent is extended or adjusted under 35 U.S.C. 154(b) by 0 days.

(21) Appl. No.: 09/378,557

(22) Filed: Aug. 19, 1999

Related U.S. Application Data

(63) Continuation-in-part of application No. 09/316,074, filed on May 20, 1999, now abandoned, which is a continuation of application No. 08/832,821, filed on Apr. 4, 1997, now Pat. No. 5,939,050, and a continuation-in-part of application No. 08/825,525, filed on Apr. 4, 1997.

(51) Int. Cl.[7] ................ A61K 7/16; A61K 7/26
(52) U.S. Cl. ................ 424/49; 424/54; 424/58; 424/405; 426/3; 426/532; 514/900; 514/902
(58) Field of Search ................ 426/3, 532; 424/49, 424/54, 58, 405; 514/900, 902

(56) References Cited

U.S. PATENT DOCUMENTS

| | | |
|---|---|---|
| 428,033 | 5/1890 | Alson et al. . |
| 1,492,299 | 4/1924 | Kyle et al. . |
| 3,787,566 | 1/1974 | Gauvreau . |
| 3,876,759 | 4/1975 | Pensak et al. . |
| 3,940,476 | 2/1976 | Haas . |
| 4,022,880 | 5/1977 | Vinson et al. . |
| 4,145,412 | 3/1979 | Ladanyi . |
| 4,406,881 | 9/1983 | Ladanyi . |
| 4,545,979 | 10/1985 | Ambike et al. . |
| 4,550,018 | 10/1985 | Ambike et al. . |
| 4,599,228 | 7/1986 | Ladanyi . |
| 4,606,911 * | 8/1986 | Hayashi et al. ........ 424/49 |
| 4,839,158 | 6/1989 | Michaels . |
| 4,894,220 | 1/1990 | Nabi et al. . |
| 4,913,895 | 4/1990 | Miyake et al. . |
| 4,933,182 | 6/1990 | Higashi et al. . |
| 4,961,924 | 10/1990 | Suhonen . |
| 4,966,754 | 10/1990 | Purohit et al. . |
| 4,992,259 | 2/1991 | Schiraldi et al. . |
| 4,999,184 | 3/1991 | Parran, Jr. et al. . |
| 5,004,597 | 4/1991 | Majeti et al. . |

(List continued on next page.)

FOREIGN PATENT DOCUMENTS

| | | |
|---|---|---|
| 0 205 133 A1 | 12/1986 | (EP) . |
| 0 227 108 * | 7/1987 | (EP) . |
| 0 605 321 A1 | 7/1994 | (EP) . |
| 0 805 198 | 11/1997 | (EP) . |
| 2 377 195 | 8/1978 | (FR) . |
| 2 743 722 | 7/1997 | (FR) . |
| 213478 | 10/1997 | (HU) . |
| 46-28430 | 8/1971 | (JP) . |
| 58-57320 | 10/1981 | (JP) . |
| 58-140014 | 8/1983 | (JP) . |

(List continued on next page.)

OTHER PUBLICATIONS

Derwent Abstract No. 007182410.
Kabara, J.J., "Aroma Preservatives: Essential Oils and Fragrances as Antimicrobial Agents," *Cosmetic and Drug Preservation: Principles and Practice*, pp. 237–273, 1984.
Kabara, J.J., "Medium–Chain Fatty Acids and Esters as Antimicrobial Agents," *Cosmetic and Drug Preservation: Principles and Practice*, pp. 274–304, 1984.

(List continued on next page.)

Primary Examiner—S. Mark Clardy
(74) Attorney, Agent, or Firm—Christensen O'Connor Johnson Kindness PLLC

(57) ABSTRACT

Gum compositions containing effective amounts of antimicrobial agents that are released to the oral cavity during chewing. In specific embodiments, the antimicrobial agents are released from the gum at different rates and times.

19 Claims, 2 Drawing Sheets

U.S. PATENT DOCUMENTS

| | | |
|---|---|---|
| 5,009,884 | 4/1991 | Suhonen . |
| 5,009,898 | 4/1991 | Sakuma et al. . |
| 5,017,363 | 5/1991 | Suhonen . |
| 5,082,653 * | 1/1992 | Pan et al. .............................. 424/54 |
| 5,094,843 | 3/1992 | Mazzanobile et al. . |
| 5,110,583 | 5/1992 | Sampathjkumar . |
| 5,135,747 | 8/1992 | Faryniarz et al. . |
| 5,145,666 | 9/1992 | Lukacovic et al. . |
| 5,190,944 | 3/1993 | Hsu . |
| 5,190,979 | 3/1993 | Herman . |
| 5,213,790 | 5/1993 | Lukacovic et al. . |
| 5,256,402 | 10/1993 | Prencipe et al. . |
| 5,268,174 | 12/1993 | Sakuma et al. . |
| 5,281,410 | 1/1994 | Lukacovic et al. . |
| 5,281,411 | 1/1994 | Majeti et al. . |
| 5,298,238 | 3/1994 | Hussein et al. . |
| 5,316,760 * | 5/1994 | Voerman .............................. 424/58 |
| 5,338,537 | 8/1994 | White, Jr. et al. . |
| 5,374,418 * | 12/1994 | Oshino et al. ........................ 424/58 |
| 5,376,374 | 12/1994 | Zelaya . |
| 5,378,465 | 1/1995 | Zeines . |
| 5,409,692 | 4/1995 | Nakahara et al. . |
| 5,453,276 | 9/1995 | Nakatsu et al. . |
| 5,468,489 | 11/1995 | Sakuma et al. . |
| 5,472,684 | 12/1995 | Nabi et al. . |
| 5,658,584 | 8/1997 | Yamaguchi . |
| 5,824,291 | 10/1998 | Howard . |
| 5,939,050 | 8/1999 | Iyer et al. . |

FOREIGN PATENT DOCUMENTS

| | | |
|---|---|---|
| 59-175410 | 10/1984 | (JP) . |
| 63-198616 | 8/1988 | (JP) . |
| 3-109314 | 5/1991 | (JP) . |
| 3-255031 | 11/1991 | (JP) . |
| 59-175410 | 1/1995 | (JP) . |
| 7-25764 | 1/1995 | (JP) . |
| 7-89819 | 4/1995 | (JP) . |
| 7-309733 | 11/1995 | (JP) . |
| 7-316064 | 12/1995 | (JP) . |
| WO 97/15277 | 5/1997 | (WO) . |
| WO 97/28805 | 8/1997 | (WO) . |
| WO 98/44901 | 10/1998 | (WO) . |
| WO 98/44926 | 10/1998 | (WO) . |
| WO 99/33352 | 7/1999 | (WO) . |

OTHER PUBLICATIONS

Mookherjec, B.D. et al., "Oils, Essential," *Encyclopedia of Chemical Technology*, 4th Ed., v. 17, pp. 603–674, 1996.

Azuma, Masahiro, Kubota, Minoru; "Aromatic bactericides preparation from hinoki oil and white cedar oil"; CA:123:3404; Apr. 4, 1995.

Kanebo Foods, Ltd.; "Anticaries agents", CA:102:31949; Oct. 4, 1984.

Yokota, Masaharu et al.; "Antimicrobial effect of aromatic natural compound, chiefly against *Staphylococcus aureus*"; CA:121–53735; ASSN:0019–1604; Igaku to Seibutsugaku; 128(3):105–10; 1994.

Doi, Tadahiro et al.; "Chloramphenicol suspension", CA:75:133025; Aug. 18, 1971.

S.S. Pharmaceutical Co., Ltd.; "Transparent liquid pharmaceuticals"; CA:99:181502; Aug. 19, 1983.

Adames, Marlene et al.; "Study of the essential oil of Eucalyptus citriodora Bailey"; CA:101:59975; ISSN:0034–7418; Inst. Roslin Przetworow Zielarskich; 4(1):95–113; 1983.

Kedzia, B. et al.; "Composition and antimicrobial characteristics of Melissa oil and its componets"; CA:121–263407; ISSN: 001890599; 40(1–2), 5–11; 1994.

Megallia, S.E. et al.; "A Study of Antimicrobial Action of Some Essential Oil Constituents"; *Herba Pol.*; 26(3):181–186; 1980.

Morris, J.A. et al.; "Antimicrobial Activity of Aroma Chemicals and Essential Oils"; *J. Am. Oil Chem. Soc.*; 56(5):595–603; 1979.

Nishida, Koichi et al.; "Anticaries glabridin and/or glabrene from *Glycyrrhiza glabra*"; CA 115:214829; Nov. 18, 1991.

Patent Cooperation Treaty International Search Report; PCT/US98/06470; Optiva Corp. et al., Aug. 20, 1998.

Marques, M.B. et al., "Comparative In Vitro Antimicrobial Susceptibilities of Nosocomial Isolates of *Acinetobacter baumannii* and Synergistic Activities of Nine Antimicrobial Combinations," Antimicrobial Agents and Chemotherapy, May 1997, vol. 1, No. 5, pp. 881–885.

* cited by examiner

GUMS CONTAINING ANTIMICROBIAL AGENTS

This application is a continuation-in-part of prior application Ser. No. 09/316,074 entitled ANTIMICROBIAL COMPOSITIONS filed on May 20, 1999 abandoned, which is a continuation of application Ser. No. 08/832,821 entitled ANTIMICROBIAL COMPOSITIONS filed on Apr. 4, 1997 now U.S. Pat. No. 5,939,050; and prior application Ser. No. 08/825,525 entitled ANTIMICROBIAL AGENTS FOR ORAL HYGIENE PRODUCTS filed on Apr. 4, 1997.

FIELD OF THE INVENTION

The present invention relates to gums and gum-like products that include antimicrobial agents capable of inhibiting the growth of oral pathogenic bacteria believed to be responsible for periodontal diseases and dental caries.

BACKGROUND OF THE INVENTION

Periodontal disease and dental caries are of major public health and economic interest worldwide. It is now widely recognized that both of these oral diseases are caused by bacteria which grow in masses on the teeth and in the gingival area. A commonly used descriptive term for these bacterial masses is "dental plaque". In the case of periodontal disease, Schluger et al. (Schluger, Yuodelis, Page & Johnson, *Periodontal Diseases*, second edition, pp. 153–262, Lea & Febiger, 1990) report that dental plaque bacteria, growing in the area where the teeth and gingival tissues meet, cause an inflammation of the gingiva called "gingivitis". This is characterized by swollen, edematous gingiva ("gums") which are reddened and bleed easily. If plaque removal is inadequate, gingivitis may progress to "periodontitis" or periodontal disease in many individuals. Periodontitis generally is characterized by a chronic inflammation of the tissues around the teeth, which leads to a resorption of supporting bone. Periodontal disease is the leading cause of tooth loss among adults. Dental caries (cavities) are also caused by bacteria, with *Streptococcus mutans* being the principal etiologic agent (McGhee, Michalek & Cassell, *Dental Microbiology*, p. 279, Harper & Row, 1982).

The prevention of dental plaque or the removal thereof has long been the focus of development, with the ultimate goal of inhibiting both caries and periodontal diseases. While the formation of dental plaque can be inhibited to a certain extent by brushing the teeth at frequent intervals, brushing alone is not sufficient to effectively prevent the formation of dental plaque or remove substantially all of the dental plaque that has formed on the teeth. Since brushing alone is often not sufficient to prevent dental caries or periodontal disease due to pathogenic plaque bacteria, chemical methods using anti-bacterials such as chlorhexidine, benzalkonium chloride, and cetylpyridinium chloride have been proposed.

In addition, the use of natural products for the treatment of teeth and gums is old in the art, having been practiced and documented since the mid-1880s. Since then, numerous patents have disclosed compositions of oral products containing natural product extracts.

There are numerous natural essential oils available. Many of these oils are described in Kirk Othmer Encyclopedia of Chemical Technology, 4th ed., vol. 17, pp. 603–674, John Wiley & Sons, Inc. Morton Pader, in "Oral Hygiene Products and Practice," *Cosmetic Science and Technology Series*, vol. 6, at pp. 356–373, Marcel Dekker, Inc., describes sanguinaria extract as an anti-plaque agent with antimicrobial properties. Pader also describes that volatile oils such as eucalyptol, menthol, thymol, methylsalicylate have varying degrees of antimicrobial activity, and antiplaque activity has been reported under appropriate test conditions. Pader describes that cinnamon oil is a very weak antiseptic, and that eucalyptus oil and eucalyptol are antiseptic. Pader notes that some essential oils are used in other products primarily for flavor. Among these are cinnamon, cassia, clove, thyme, peppermint, anise and anethol. Pader also describes that these essential oils have detectable antimicrobial activity.

It is known that hinokitiol, citral, geraniol, cocamidopropyl betaine, berberine, and juniper berries oil, individually exhibit antimicrobial properties against certain bacteria.

U.S. Pat. No. 3,940,476 describes a method for inhibiting the formation of dental plaque, which comprises topically applying to the teeth as an active ingredient an amount of either one or a combination of (a) allyl isothiocyanate, (b) uranine, (c) obtusastyrene, (d) citral, (e) citronellol, (f) nerol, or (g) geraniol.

U.S. Pat. No. 4,913,895 describes an oral composition including a linear polyphosphate or a cyclic polyphosphate and menthol, anethol, or mixtures thereof in an aqueous medium. The composition is reported to have antibacterial effects and prevent the development of calculus and periodontal diseases.

U.S. Pat. No. 4,966,754 describes that certain essential oils and combinations thereof possess antimicrobial properties against *Aspergillus niger, Candida albicans, Staphylococcus aureus*, and *Pseudomonas aeruginosa* and therefore are useful as preservatives in cosmetic compositions. A blend of 14 essential oils is described as providing desirable antimicrobial properties against the noted microorganisms. The described combination is disclosed as being suitable as a preservative for cosmetic compositions.

U.S. Pat. No. 4,999,184 describes oil compositions containing certain pyrophosphate salts which are reported to provide an anticalculus benefit.

U.S. Pat. No. 5,316,760 describes a mouthcare product that contains a combination of *Urtica dioica* extract and an extract of *Juniperus communis*. The combination of these extracts is described as leading to a synergistic reduction of both dental plaque and bleeding or inflammation of the gingiva. *Achillaea millefolium* extract is also described as being a suitable additive to the combination of the *Urtica dioica* and *Juniperus communis* extracts.

U.S. Pat. No. 5,472,684 describes a composition including thymol and eugenol, and optionally a sesquiterpene alcohol, such as farnesol, that reportedly has antiplaque and antigingivitis effects. Australian tea tree oil, sage oil, and eucalyptol are described as enhancing the antiplaque and antigingivitis activity of mouth rinses formulated from the disclosed compositions.

JP Publication 03-109314 describes a chemically stable anticarious agent containing glabridin and glabrene as an active ingredient that is obtained by extracting licorice root with an organic solvent having a medium polarity. Benzene, ethyl ether, chloroform, methylene chloride, ethyl acetate, n-butyl acetate, isobutyl acetate and n-propyol acetate are described as suitable medium polarity solvents. JP 58-57320 describes a methanol extract of Glycyrrhiza as a plaque suppressant. JP 63-198616 describes an anticariogenic substance including gymnemic acid in combination with glycyrrhizin extracted from the root of *Glycyrrhiza glabra*. JP 3-255031 describes a composition for preventing gingival disease that contains a thyme extract and a purified oil or oleoresin, such as rosemary oil. JP 59-175410 describes an antiseptic agent containing a natural essential oil or a natural essential oil in combination with another antiseptic substance. Rosemary oil, lemon oil, citronella oil, and basil oil are described as natural essential oils. Citral and geraniol are described as an antiseptic substance.

One property that characterizes the effectiveness of an antimicrobial agent as an antiplaque and anticalculus agent is the minimum inhibitory concentration, or MIC, of the agent. The MIC is the minimum concentration in micrograms per milliliter of an antimicrobial agent at which no bacterial growth is observed. At concentrations below the MIC, an antimicrobial agent is ineffective at killing or inhibiting the growth and reproduction of bacteria. At concentrations above the MIC, an antimicrobial agent is effective at killing or inhibiting the growth and reproduction of bacteria.

Typically, antimicrobial agents are introduced into the oral cavity at an initial concentration. Almost immediately, the initial concentration begins to decrease due to the dynamics of the oral cavity. Eventually, the concentration of the antimicrobial agent within the oral cavity will fall below the MIC. Thus, it has been a goal of those working to develop antiplaque and anticalculus formulations to use antimicrobial agents that have low MICs.

One method of introducing antimicrobial agents to the oral cavity has been to use a dentifrice or a mouthwash or rinse as a delivery mechanism. While these vehicles can provide satisfactory delivery of antimicrobial agents to the oral cavity, individuals do not necessary use these type of products on a systematic, regular basis. In addition with brushing or rinsing, the length of time that the antimicrobial agents are in contact with the oral cavity is related to the length of time that the dentifrice or rinse remains in the oral cavity. While there may be residual amounts of antimicrobial agents that remain in the oral cavity after rinsing away of the dentifrice or expulsion of the rinse, generally the length of contact time is relatively short, for example on the order of one to three minutes. There continues to be a need for alternative methods for delivering antimicrobial agents to the oral cavity to supplement the benefits of brushing and using mouthrinses. By developing additional methods of delivering antimicrobial agents to the oral cavity, additional opportunities can be provided to individuals who would like to increase the frequency of the application of antimicrobial agents to the oral cavity without additional brushing or use of mouthrinses. In addition, such alternative methods may extend the time during which the antimicrobial agents are maintained in contact with the oral cavity.

SUMMARY OF THE INVENTION

In one aspect, the present invention relates to a gum composition which includes at least two antimicrobial agents selected from the group consisting of berberine, cedarwood oil, chloramphenicol, *Glycyrrhiza glabra* extract, juicy fruit basil oil, juniper berries oil, and lemon basil oil. In another embodiment, the present invention relates to a gum composition that includes an antimicrobial agent selected from the group consisting of cedarwood oil, chloramphenicol, *Glycyrrhiza glabra* ethanol extract, juicy fruit basil oil and lemon basil oil. Gums formed in accordance with the present invention are used to deliver antimicrobial agents to the oral cavity and release the agents to the oral cavity at concentrations that are above the MIC for the agents. Accordingly, the chewing of a gum formed in accordance with the present invention provides an alternative to brushing or mouthwashes as a means for combating the formation of dental plaque. Antimicrobial agents useful in accordance with the present invention include berberine, cedarwood oil, chloramphenicol, *Glycyrrhiza glabra* extract, juicy fruit basil oil, juniper berries oil, and lemon basil oil. In addition, geraniol and cocamidopropyl dimethylglycine can be used as antimicrobial agents in accordance with the present invention.

In accordance with the present invention, applicants have observed that certain antimicrobial agents are released from a gum base at a different rate than other antimicrobial agents. Based on this observation, the present invention provides a gum composition that comprises a first antimicrobial agent that is released from a gum base to the oral cavity to provide a concentration in the oral cavity above the MIC of the first antimicrobial agent within about one to five minutes of initiation of gum chewing. This preferred gum composition also includes a second antimicrobial agent that is released from the gum base to the oral cavity to provide a concentration in the oral cavity above the MIC of the second antimicrobial agent after about five minutes from initiation of gum chewing. Gum compositions formed in accordance with the present invention which include these two types of antimicrobial agents provide a gum that is able to deliver antimicrobial agents to the oral cavity and maintain a concentration of at least one of the antimicrobial agents above the MIC for an extended period of time, preferably on the order of about 25 minutes or longer.

In another aspect, the present invention also relates to a method of inhibiting the growth of oral pathogenic bacteria in the oral cavity by releasing certain antimicrobial agents from a gum into the oral cavity. The present invention also provides methods of manufacturing a gum which involves the incorporation of certain antimicrobial agents into a gum base.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
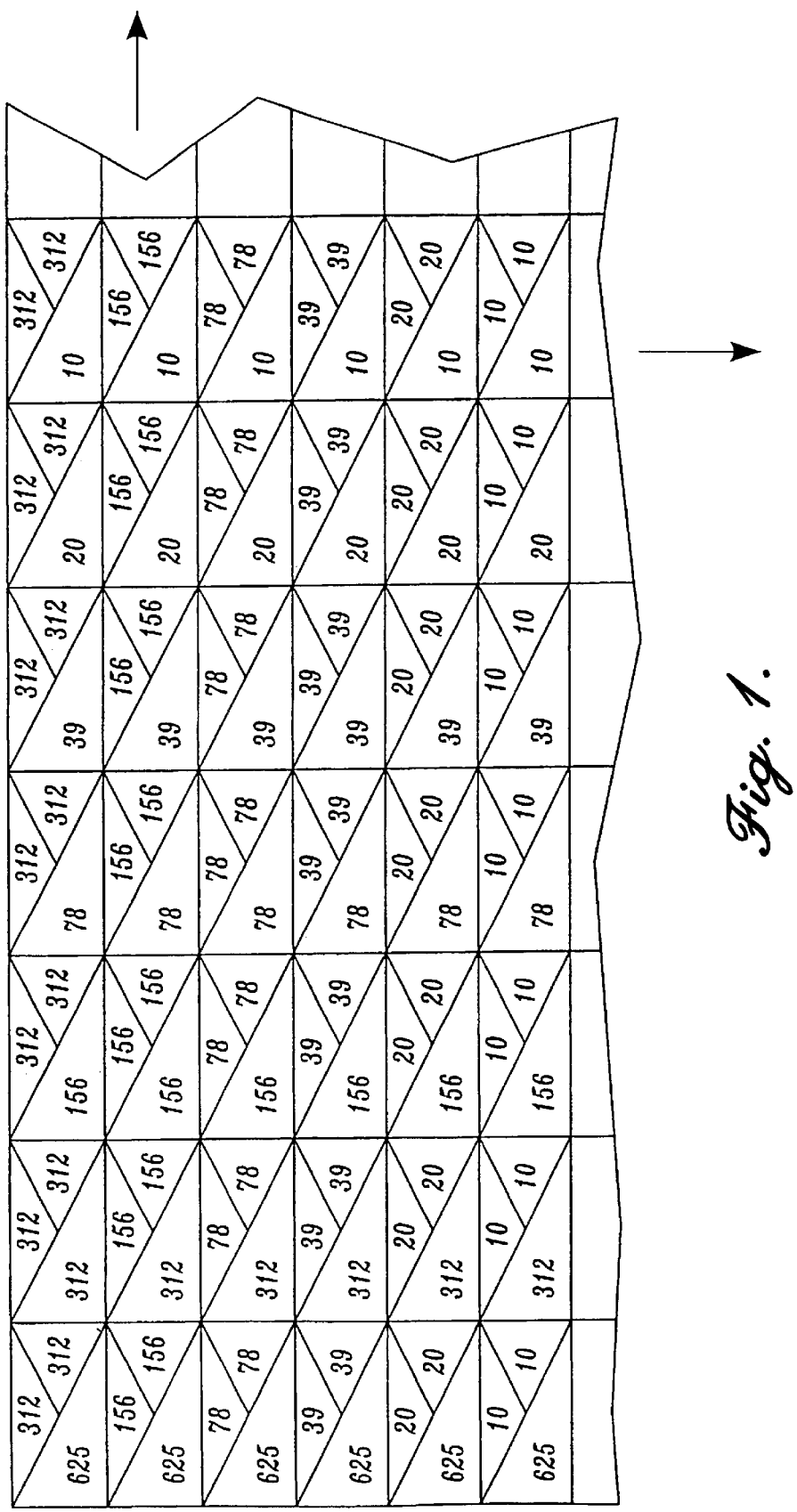
FIG. 1 is a schematic illustration of the dilution scheme in a 96 well plate for a combination of three antimicrobial agents A, B, and C.

As used herein, the following terms have the following meanings.

"Berberine" refers to 5,6-dihydro-9,10-dimethoxybenzo[g]-1,3-benzodioxolo [5,6-a] quinolizinium and salts thereof. Berberine is an alkaloid isolated from *Hydrastis canadensis* L. and several other plants in the Berberidaceae family. Exemplary salts of berberine include berberine hydrochloride, berberine bisulfate, and berberine sulfate. The Chemical Abstract Service Registry (CAS) number for berberine is 84603-60-1.

"Cedarwood oil" refers to volatile whole oil extracts derived principally from the heartwood of *Juniperus virginiana* or *Juniperus ashei*. Constituents of the whole oil extract include thujopsene, cedrol, alpha-copaene, alpha-cedrene, beta-cedrene and widdrol. A preferred cedarwood oil is red cedarwood oil. The CAS number for cedarwood oil is 8000-27-9.

"Chloramphenicol" refers to 2,2-dichloro-N-[2-hydroxyl-1-(hydroxymethyl)-2-(4-nitrophenyl) ethyl]acetamide. Chloramphenicol is derived from *Streptomyces venezuelae* or by organic synthesis. The CAS number for chloramphenicol is 56-75-7.

"Geraniol" refers to trans-3,7-dimethyl-2,6-octadien-1-ol. The CAS number for geraniol is 106-24-1. Geraniol is found as a constituent in other essential oils such as citronella, lemon grass, rose oil, and palmarosa.

"N-cocamidopropyl-dimethylglycine" has a CAS number of 61789-40-0, 83138-0-3, and 86438-79-1.

"*Glycyrrhiza glabra* extract", also known as licorice root extract, refers to the crude powder extract from *Glycyrrhiza glabra*. Several varieties including *G. typica* and *G. glandulifera* exist. *Glycyrrhiza glabra* extract includes as constituents glycyrrhizic acid and glycyrrhetinic acid. Glycyrrhizic acid can be isolated from *Glycyrrhiza glabra* root and used independently in accordance with the present invention. The whole extract is available from commercial sources or may be collected by solvent extraction, such as the ethanol extraction described below. The ethanol extraction is preferred over other types of extraction methods such as methanol and other medium polarity solvents because of the generally accepted safety of ethanol compared to these other solvents.

"Juicy fruit basil oil" refers to the whole extract of a selected variety of basil with a juicy fruit component. Juicy fruit basil is a cultivar of *Ocimum basilicum* L.

"Juniper berries oil" refers to volatile whole oil extract from the dried ripe fruit of *Juniperus communis*, Cupressaceae family. Juniper berries oil is also known as extract of Juniper, extract of *Juniperus communis*, and Juniper extract. The CAS number for Juniper berries oil is 84603-69-0.

"Lemon basil oil" refers to the volatile whole oil extract from a selected variety of basil with a citral component. Lemon basil is a cultivar of *Ocimum basilicum* L with a high content of citral.

"*Rosmarinus officinalis* oil" refers to the whole oil extract from the flowering tops of *Rosmarinus officinalis*. *Rosmarinus officinalis* oil is also known as the extract of Rosemary, or the extract of *Rosmarinus officinalis* oil. The CAS number for *Rosmarinus officinalis* oil is 84604-14-8.

Additional information regarding the essential oils described above can be found in Kirk-Othmer Encyclopedia of Chemical Technology, Fourth Edition, Volume 7, pages 603–674, John Wiley & Sons, Inc.

All of the foregoing are available from commercial sources.

"Minimal inhibitory concentration or MIC" refers to the minimum concentration in micrograms per milliliter of an antimicrobial agent at which no bacterial growth are observed. At concentrations below the MIC, the antimicrobial agent is ineffective at killing or inhibiting the growth and reproduction of bacteria. At concentrations above the MIC, the antimicrobial agent is effective at killing or inhibiting the growth and reproduction of bacteria.

Gum compositions formed in accordance with the present invention comprise specific antimicrobial agents as described below and conventional components such as chewing gum base, sugar, corn syrup, softeners, and flavorings. In sugar-free gums, aspartame, mannitol, xylitol, and sorbitol often replace sugar and corn syrup.

The gum base gives the gum a smooth, soft texture and acts as a base that binds together all the other ingredients. Typical sources of gum base include various natural resins and latexes such as chicle, sorva and jelutong. As these sources of natural resins and latexes become more scarce, the use of naturally derived rosins and softeners in a base have been used. The primary function of the rosin is to enhance the texture of the gum base. Suitable rosins can be found in pine trees of southeastern and the southern parts of the United States. These rosins and softeners serve to soften and improve the texture of synthetic gum based materials that have been developed to replace the diminishing supplies of natural resins and latexes.

Suitable sweeteners used to enrich the flavor of the gum base include pure powdered cane and beet sugar and corn syrup. In sugar free gum, aspartame is used as a highly concentrated sweetener, in addition to sucrose, glucose, malitol, xylitol, sorbitol and mannitol and other mixtures thereof.

As softeners, glycerin, lecithin, and other vegetable oil products can be included in the gum base. The softeners help to blend other ingredients into the gum base and keep the gum soft and flexible by retaining a proper amount of moisture in the gum.

Common flavorings that are included in chewing gum are derived from mint plants such as spearmint and peppermint. Other sources of flavorings include those derived from a variety of fruit and spice essences. It should be understood that the non-active components of the gum composition can vary from that described herein without departing from the present invention which relates to the inclusion of antimicrobial agents in the gum composition.

The gum can be formed using conventional techniques which involve grinding the base materials first. Next, the base material is melted and purified through high speed centrifuges and filter machines. When still hot, the base material goes to mixers where additional ingredients such as sweeteners and flavors are added. The antimicrobial agents may be added at this juncture or at any other juncture, provided subsequent processing does not adversely affect their antimicrobial properties. After incorporation of the sweeteners and flavors, the gum is sent through a series of rollers that form it into a thin, wide ribbon. A light coating of finely powdered sugar or sugar substitute is added during this rolling process to keep the gum from sticking and to enhance the flavor. This continuous ribbon of gum is then scored in a pattern of single sticks.

The scored gum ribbon is then conditioned under carefully controlled temperature and humidity conditions to ensure that the gum cools to make sure that it will remain fresh on store shelves. The conditioned gum is then packaged.

A gum composition as described above, useful as an oral hygiene product formed in accordance with one aspect of the present invention includes an antimicrobial agent selected from cedarwood oil, chloramphenicol, *Glycyrrhiza glabra* ethanol extract, juicy fruit basil oil, and lemon basil oil. The gum composition upon being chewed releases the antimicrobial agents into the oral cavity where the antimicrobial agent serve to inhibit the growth of oral pathogenic bacteria.

Preferred gum compositions include an antimicrobial agent selected from cedarwood oil, chloramphenicol, and *Glycyrrhiza glabra* ethanol extract. The preferred antimicrobial agents are selected because these agents are surprisingly effective at retarding the growth of and/or preventing the growth of representative gram-positive and gram-negative oral pathogenic bacteria such as *Actinomyces viscosus, Fusobacterium nucleatum, Porphyromonas gingivalis, Streptococcus mutans,* and *Streptococcus sanguis.* The examples that follow illustrate the effectiveness that the antimicrobial agents of the present invention have against these particular bacteria. Preferably, the antimicrobial agent is effective against more than one of the bacteria noted above, and preferably all of the bacteria noted above.

The particular amount of antimicrobial agent present in gum compositions formed in accordance with the present invention is not limited to any particular value, provided that the amount present is effective to provide an antimicrobial agent concentration in the oral cavity after chewing that is effective at retarding the growth of bacteria and/or preventing the growth of bacteria, i.e., an amount that is greater than the MIC of the antimicrobial agent with respect to the particular bacteria. In order to ensure that the concentration in the oral cavity of the antimicrobial agent released from the gum is greater than the MIC for the particular agent, the concentration of the antimicrobial agent in the gum composition can be chosen so as to provide such desirable concentration in the oral cavity. Generally, to provide a concentration of antimicrobial agent in the oral cavity greater than the MIC, concentration of the antimicrobial agent in the gum should be greater than the MIC for that agent. When considering an upper limit as to the amount of antimicrobial agent to be included in the gum, consideration should be given to the effect that the antimicrobial agent has on the organoleptic properties of smell, taste of the gum, up front flavor release, and prolonged flavor release, and its other important properties, such as texture, tackiness, mouth feel, and chew.

As illustrated in the examples that follow, the individual antimicrobial agents described above are useful in the gum compositions of the present invention exhibit MICs that range from about 3.1 to about 156 against the representative oral pathogens *Actinomyces viscosus, Fusobacterium nucleatum, Porphyromonas gingivalis, Streptococcus mutans,* and *Streptococcus sanguis.*

In accordance with another aspect of the present invention, gum compositions of the present invention include combinations of antimicrobial agents, some of which include those described above that exhibit a surprising synergistic and unexpectedly significant decrease in the MIC of at least one, and preferably all of the antimicrobial agents in the combination compared to the MIC of a specific agent of the combination alone, i.e., in the absence of the other agents. This surprising reduction in MIC has been observed relative to representative gram-positive and gram-negative oral pathogenic bacteria such as *Actinomyces viscosus, Fusobacterium nucleatum, Porphyromonas gingivalis, Streptococcus mutans, Streptococcus sanguis* and *Campylobacter rectus.* For example, if the MIC for agent A alone is 10 and the MIC for agent B alone is 20, in accordance with the present invention, when agent A and agent B are combined, the MIC of agent A in the presence of agent B decreases relative to the MIC of agent A alone. Furthermore, preferably, the MIC of agent B in the presence of agent A decreases relative to the MIC of agent B alone. This reduction in the MIC of agent A and of agent B in the combination translates into the ability of agent A, and preferably agent B, to inhibit and/or prevent the growth and reproduction of bacteria at lower concentrations of antimicrobial agents A and B, compared to if only antimicrobial agent A or only antimicrobial agent B were present. As described in the background of the invention, typically the concentration of antimicrobial agents decreases from the time that the agents are initially applied to the oral cavity. Thus, by effectively lowering the MIC of an antimicrobial agent, the period of time during which that antimicrobial agent can be expected to inhibit or prevent the growth of bacteria is extended. The surprising and unexpected results will be described in more detail below and illustrated in the examples that follow.

Combinations of antimicrobial agents useful in gum compositions of the present invention include: (1) an antimicrobial agent A selected from berberine, cedarwood oil, chloramphenicol, cocamidopropyl dimethylglycine, *Glycyrrhiza glabra* extract, juicy fruit basil oil, juniper berries oil, and lemon basil oil; and (2) an antimicrobial agent B different from antimicrobial agent A selected from the same list. In addition, combinations useful in the gum formulations of the present invention include geraniol and an antimicrobial agent selected from berberine, cedarwood oil, chloramphenicol, cocamidopropyl dimethylglycine, *Glycyrrhiza glabra* extract, juicy fruit basil oil, juniper berries oil, and lemon basil oil.

Of the many combinations of antimicrobial agents set forth above, preferred combinations include cedarwood oil and an antimicrobial agent selected from berberine, chloramphenicol, cocamidopropyl dimethylglycine, geraniol, *Glycyrrhiza glabra* extract, and juicy fruit basil oil. Most preferred are combinations of cedarwood oil with berberine, chloramphenicol, cocamidopropyl dimethylglycine, geraniol, and *Glycyrrhiza glabra* extract.

Another preferred set of combinations includes berberine and an antimicrobial agent selected from chloramphenicol, geraniol, *Glycyrrhiza glabra* extract, juicy fruit basil oil, juniper berries oil, and lemon basil oil. Most preferred for combination with berberine are chloramphenicol, geraniol, *Glycyrrhiza glabra* extract, and lemon basil oil.

Preferred results are obtained when *Glycyrrhiza glabra* extract is combined with antimicrobial agents selected from cedarwood oil, chloramphenicol, geraniol, juicy fruit basil oil, juniper berries oil, and lemon basil oil, lemon oil. Most preferred for combination with *Glycyrrhiza glabra* extract are antimicrobial agents selected from cedarwood oil, geraniol, and juniper berries oil.

The foregoing combinations of the noted antibacterial agents are preferred and most preferred because of. (1) the degree to which the MIC of the individual antimicrobial agents in the combination is reduced compared to the MIC of those agents when evaluated alone; and (2) the MIC for the individual antimicrobial agents that is achieved due to the combination of agents.

In addition to compositions that include two antimicrobial agents as described above, the gum compositions of the present invention can also include more than two, such as three or four antimicrobial agents wherein the MIC of at least one, and preferably all, of the constituent agents in the combination is reduced compared to the MIC of those constituents determined alone. Accordingly, an antimicrobial agent C selected from the groups set forth above wherein antimicrobial agent C is different from agent A and agent B and can be added to agent A and agent B to provide a three component composition in accordance with the present invention. Combinations of antimicrobial agents A, B and C provide compositions wherein the MIC of at least one, and preferably all of the constituent agents, is reduced compared to the MIC of those constituents determined alone. In addition, in some instances, the MIC of the constituents in the combination of three antimicrobial agents is reduced relative to the MIC of various pairings of the three constituent agents.

The ratio of antimicrobial agents in gum compositions formed in accordance with the present invention is not limited to any particular values provided that the gum compositions when chewed provide a concentration of an antimicrobial agent in the oral cavity that is greater than the MIC and preferably the reduction in the MIC of the antimicrobial agent combination is achieved as described above. Ratios for the two component compositions ranging from about 500:1 to about 1:500 have been observed to provide surprising and unexpected reductions in the MICs. In the three component system, any one agent can relate to the other two agents in a range from about 500:1 to about 1:500 to provide reductions in the MIC.

As described above, the particular amount of antimicrobial agent present in gum compositions formed in accordance with the present invention is not limited to any particular value, provided that the amount present in the gum is effective to allow for the release of sufficient amounts of the agents into the oral cavity so that the concentration of the agents in the oral cavity are effective at retarding the growth of bacteria and/or preventing the growth of bacteria, i.e. in an amount that is greater than the MIC of the antimicrobial agent with respect to the particular bacteria. Suitable amounts range from about 0.001 wt. % to about 4 wt. %, preferably about 0.005 wt. % to about 2.0 wt. % for each agent based on the total weight of the gum composition containing the antimicrobial agents. The foregoing amounts are preferred because they provide a gum composition that includes a sufficient amount of antimicrobial agents that can be released to the oral cavity and provide a antimicrobial agent concentration in the oral cavity above the MIC for that antimicrobial agent. In addition, the above amounts are preferred because they do not adversely affect the organoleptic properties of the gum base.

The gum compositions formed in accordance with the present invention are used by individuals chewing the gum to release the antimicrobial agents. Components of gum compositions of the present invention, other than the antimicrobial agents, are preferably selected so that they do not have an antagonistic effect on the MIC lowering aspect of the antimicrobial compositions incorporated into the gum compositions.

When selecting specific antimicrobial agents from the lists provided above consideration should be given to the release characteristics of the particular antimicrobial agent from the gum base. If the antimicrobial agent is not effectively released by the gum composition upon chewing, then the agent will not be present in the oral cavity in any substantial amount, let alone a concentration above the MIC. Furthermore, it is preferred that the gum composition maintain a concentration of antimicrobial agent in the oral cavity over a sustained period of time. An antimicrobial agent that is released in a manner that provides a concentration in the oral cavity above the MIC for that agent over a longer period of time compared to another antimicrobial agent which provides a higher concentration but for a shorter period of time, may be preferred, or vica versa. Alternatively, a combination of antimicrobial agents can be selected so that the concentration of at least one of the antimicrobial agents in the oral cavity is above the MIC during a given period of time after chewing of the gum has commenced. These periods of time when concentrations of the antimicrobial agents in the oral cavity are above the MIC can overlap or be sequenced in time.

In a preferred embodiment of the present invention, the specific antimicrobial agents that are employed in the gum formulation are chosen so that their release from the gum base complements each other with respect to the time domain. In other words, if two antimicrobial agents are incorporated into a gum in accordance with this preferred aspect of the present invention, it is preferred that one agent be released more quickly from the gum base than the other agent. By selecting the agents accordingly, not only can the MIC reducing characteristics of the agents in combination be exploited, the time period during which the concentration of at least one of the antimicrobial agent is above the MIC in the oral cavity is preferably extended. By extending the time period where the concentration of at least one of the antimicrobial agents is above the MIC in the oral cavity, the antimicrobial effectiveness of the gum can be prolonged.

As a general guide to selecting combinations of antimicrobial agents that are released from a gum base in sequence relative to the time domain, agents should be selected so that one agent is released more quickly than another agent. Without intending to be bound by theory, it is believed that the release characteristics of a particular agent relative to another agent can be predicted based on the hydrophilicity of one agent relative to another. For example a gum base that is slightly hydrophilic, such as a standard peppermint gum base, will tend to release a less hydrophilic antimicrobial agent more quickly than an antimicrobial agent that is more hydrophilic. Accordingly, in accordance with the present invention, a gum composition formed in accordance with the present invention, preferably includes antimicrobial agents that exhibit differing levels of hydrophilicity. In accordance with a preferred embodiment of the present invention, in a gum composition comprising cedarwood oil and *Glycyrrhiza glabra* extract, the cedarwood oil is a less hydrophilic agent and the *Glycyrrhiza glabra* extract is a more hydrophilic agent. Other antimicrobial agents such as geraniol tend to be more hydrophilic compared to either cedarwood oil or *Glycyrrhiza glabra* extract and thus tend to be released at a rate that is slower than the rate that the cedarwood oil and *Glycyrrhiza glabra* extract are released. Of the other antimicrobial agents that can be incorporated into a gum in accordance with the present invention, berberine and chloramphenicol are more hydrophilic than glycyrrhizic acid. Juicy fruit basil oil and lemon basil oil are slightly more hydrophilic than glycyrrhizic acid and less hydrophilic than *Glycyrrhiza glabra* extract.

Cedarwood oil, *Glycyrrhiza glabra* extract and glycyrrhizic acid are examples of antimicrobial agents that can be released from a gum composition and maintain a concentration in the oral cavity at a level above the MIC for the individual agent. Gum compositions that include one of these antimicrobial agents are within the scope of the present invention. Examples 5 and 6 describe gum compositions and the release characteristics of such gum compositions including these agents and various combinations of these antimicrobial agents and others.

The present inventors observed that certain agents such as cedarwood oil are readily released from a gum composition soon after chewing of the gum begins as evidenced by a sudden increase in the concentration of cedarwood oil in the oral cavity to above its MIC; however the concentration of cedarwood oil in the oral cavity drops off to below its MIC within about one to five minutes of initiation of chewing. Accordingly, cedarwood oil is preferred as an antimicrobial agent that provides a concentration in the oral cavity above its MIC soon after chewing of the gum has begun.

In contrast other antimicrobial agents such as *Glycyrrhiza glabra* extract, glycyrrhizic acid and geraniol are released from a gum base less quickly and over a longer period of time. Accordingly, while these agents can be released from a gum base in quantities sufficient to provide a concentration in the oral cavity above the MIC for the specific agent, these agents achieve such a concentration at a slower rate compared to the more quickly released agents such as cedarwood oil. *Glycyrrhiza glabra* extract is an example of an antimicrobial agent capable of being released into the oral cavity and maintaining a concentration above its MIC for at least about 25 minutes. Geraniol exhibits a similar substantivity in the oral cavity and can maintain a presence in the oral cavity for periods on the order of 25 minutes. In accordance with the present invention, in the preferred embodiment, a more quickly released antimicrobial agent is combined with a more slowly released antimicrobial agent, i.e., one which is released by a gum base in an amount that provides a concentration in the oral cavity above the MIC for that antimicrobial agent after about five minutes from initiation of chewing is preferred. *Glycyrrhiza glabra* extract, glycyrrhizic acid, and geraniol are examples of antimicrobial agents that are released from a gum base more slowly than cedarwood oil. *Glycyrrhiza glabra* extract and glycyrrhizic acid are examples of more slowly released agents that can be released from a gum base and provide a concentration in the oral cavity above the MIC for the particular agent.

In a preferred embodiment a gum formulation formed in accordance with the present invention includes an antimicrobial agent, such as cedarwood oil, that is released quickly from the gum base to rapidly provide a concentration in the oral cavity of an antimicrobial agent above its MIC, and an antimicrobial agent, such as *Glycyrrhiza glabra* extract, glycyrrhizic acid or geraniol, that is released less rapidly. *Glycyrrhiza glabra* extract and glycyrrhizic acid are preferred slow release agents since each of them is able to provide a concentration in the oral cavity above the MIC after the concentration of the more quickly released agent in the oral cavity has subsided to below its MIC.

While the more quickly released antimicrobial agents have been described above by way of cedarwood oil as an example, it should be understood that other agents that provide similar release characteristics would be suitable. Likewise, antimicrobial agents in addition to the ones described above as being more slowly released could be used. The specific selection of particular antimicrobial agents will depend on the particular release characteristics of the particular agents and when it is desired to have such agents be present in the oral cavity at a concentration above their MIC.

The following Examples 1 and 2 illustrate the surprising and unexpected reduction in the MIC of the antimicrobial components useful in gum compositions for inhibiting the growth of bacteria in the oral cavity formed in accordance with the present invention.

EXAMPLE 1

Determination of Minimum Inhibitory Concentration of Individual Agents and Two Antimicrobial Agents in Combination The following example illustrates how the MIC of individual antimicrobial agents that are combined were determined and also illustrates how the MIC of the antimicrobial agents in combination were determined.

A microtiter plate was used to dilute the antimicrobial agents to varying concentrations in order to determine the MIC of those antimicrobial agents alone and the MIC of the agents when combined.

A bacterial culture was incubated at 37° C. Prior to the dilution of the antimicrobial agents as described below, the bacterial culture was spun down at 2,000 rpm into a pellet and resuspended in a solution of buffered phosphate. The innoculum was normalized with a spectrophotometer to an optical density at 550 nanometers of between 0.180–0.220 (equivalent to $5.0 \times 10^7$ colony forming units, CFU per milliliter). The innoculum was set aside until the completion of the antimicrobial agent dilution.

A sterile polystyrene 96-well plate was used to dilute combinations of antimicrobial agent A and antimicrobial agent B. Using aseptic technique, 100 microliters of distilled water was placed in each test well. The dilution scheme of the antimicrobial agents was separated into two parts, the first part being the dilution of agent A and the second part being the dilution of agent B. One hundred microliters of stock solution for agent A was placed in the first well of each column. This was a one-half dilution based on the concentration of the stock solution. One hundred microliters was then transferred to the next well and so on down each of the test wells. Each transfer was a one-half dilution of the preceding well concentration. One hundred microliters of agent B stock solution was then added to the first well of each row and diluted across the plate in the same manner that agent A was diluted down the plate. After the dilution of agent B was completed, 80 microliters of growth media specific for the bacteria under study was added to each well.

In one column of the plate, 100 microliters of stock solution for agent A was placed in the first well. 100 microliters was then transferred to the next well and so on down each of the test wells in the column. Each transfer was a ½ dilution of the preceding well concentration of agent A. The foregoing was replicated in another column using agent B. These two columns were used to determine the MIC for agent A alone and agent B alone. After dilution of agent A alone and agent B alone was completed, 80 microliters of growth media specific for the bacteria under study was added to each well in these two columns.

Twenty microliters of innoculum was then added to each well. This resulted in the first well having a final dilution of one-quarter based on the concentration of the stock solutions. The remaining wells were a one-half dilution of the preceding well for each transfer. The 96-well plate was incubated under conditions that varied based on the particular microorganism. The aerobic bacteria *Actinomyces viscosus*, *Streptococcus mutans* and *Streptococcus sanguis* were incubated under ambient room conditions. The anaerobic bacteria *Fusobacterium nucleatum* and *Porphyromonas gingivalis* were incubated under an atmosphere of 10% hydrogen, 5% carbon dioxide and the balance nitrogen gas.

Following 48 hours of incubation, the incubated plate was read for microbial growth with a spectrophotometer by optical density (OD). The well containing the lowest dilution achievable for each agent with a spectrophotometer reading below 0.05 OD (i.e., no detectable microbial growth) was considered representative for the combination. The MIC for each agent in the combination was determined by accounting for the starting stock solution concentration and the resulting dilutions in the 96-well plate.

The specific bacteria inoculated into the 96-well plate are set forth in Table 1 below along with the growth media and the incubation conditions for that microorganism.

TABLE 2

Microorganisms/Growth Media/Incubation Conditions

| Microorganism | ATCC No. | Growth Media | Incubation Conditions |
|---|---|---|---|
| Actinomyces viscosus (AV) | 19246 | TSB[1] | 48 hrs/37° C./aerobic |
| Fusobacterium nucleatum (FN) | 10933 | FN media[3] | 48 hrs/37° C./anaerobic |
| Porphyromonas gingivalis (PG) | 33277 | PG media[2] | 48 hrs/37° C./anaerobic |
| Streptococcus mutans (SM) | 25175 | TSB[1] | 48 hrs/37° C./aerobic |
| Streptococcus sanguis (SS) | 49295 | TSB[1] | 48 hrs/37° C./aerobic |

[1] Tryptic Soy Broth 3.0% wt. to vol., yeast extract 0.1%, and 999 milliliters distilled water.
[2] Tryptic Soy Broth 3.0% wt. to vol., yeast extract 0.5%, L-cystein 0.05%, Hemin 0.0005%, Menadione 0.00002%, and 990 milliliters distilled water.
[3] Tryptic Soy Broth 3.0% wt. to vol., yeast extract 0.5%, Peptone 1.0%, L-cystein extract, Hemin 0.0005%, Menadione 0.00002%, and 990 milliliters distilled water.

The antimicrobial agents from which agent A and agent B were selected are set forth in Table 2 below.

TABLE 2

| | |
|---|---|
| Berberine hydrochloride | (BX1) |
| Cedarwood oil | (RC1) |
| Chloramphenicol | (CR1) |
| Cocamidopropyl dimethylglycine | (TB1) |
| Geraniol | (GRA1) |
| Glycyrrhiza glabra ethanol extract | (GLY) |
| Juicy fruit basil oil | (JFB1) |
| Juniper berries oil | (JPE1) |
| Lemon basil oil | (LMB1) |

In the following tables, the respective antimicrobial agents A and B are identified with respect to the abbreviations set forth in Table 2. In addition, the five microorganisms set forth in Table 1 are referred to by the abbreviations set forth in Table 1.

Various combinations of the antimicrobial agents set forth in Table 2 were evaluated in accordance with the protocol set forth above in order to identify combinations of agents that will inhibit visible in vitro growth of microorganisms and evaluate the MIC of the agents in the combination. In addition, the lowest concentration, e.g., (MIC), of each of the antimicrobial agents used in the two component combinations that inhibited visible in vitro growth of a particular microorganism was determined in accordance with the protocol set forth above. The resulting data are summarized in Tables 3–11. In each of these tables, a mean MIC value is given for agent A alone. Because multiple well plates were inoculated and incubated in accordance with the procedure above in order to ascertain the information regarding the multiple combinations, in each run, a MIC for agent A alone was determined. The MIC for agent A alone given in Tables 3–11 represents the mean of these values.

TABLE 3

MIC of Cedarwood Oil Alone and in Combination with Antimicrobial Agent B

| Agent | | MIC (μg/ml) of Cedarwood Oil When Combined With Agent B for Identified Bacteria | | | | |
|---|---|---|---|---|---|---|
| A | B | AV | FN | PG | SM | SS |
| RC1 | — | 36.5 | 36.5 | 7.8 | 31.3 | 15.6 |
| | +BX1 | 7.8 | 2.0 | 2.0 | 7.8 | 2.0 |
| | +CR1 | 7.8 | 3.9 | 2.0 | 2.0 | 7.8 |
| | +TB1 | 7.8 | 15.6 | 2.0 | 7.8 | 31.3 |
| | +GRA1 | 3.9 | 7.8 | 2.0 | 7.8 | 2.0 |
| | +GLY | 7.8 | 15.6 | 3.9 | 7.8 | 3.9 |
| | +JFB1 | 7.8 | 15.6 | 3.9 | 2.0 | 3.9 |
| | +JPE1 | 2.0 | 15.6 | 3.9 | 7.8 | 7.8 |
| | +LMB1 | 2.0 | 2.0 | 3.9 | 7.8 | 3.9 |

TABLE 4

MIC of Berberine Hydrochloride Alone and in Combination With Antimicrobial Agent B

| Agent | | MIC (μg/ml) of Berberine Hydrochloride When Combined With Agent B for Identified Bacteria | | | | |
|---|---|---|---|---|---|---|
| A | B | AV | FN | PG | SM | SS |
| BX1 | — | 31.9 | 38.5 | 11.4 | 43.3 | 46.9 |
| | +RC1 | 3.9 | 15.6 | 7.8 | 3.9 | 7.8 |
| | +CR1 | 3.9 | 15.6 | 7.8 | 2.0 | 3.9 |
| | +TB1 | 31.3 | 31.3 | 7.8 | 31.3 | 15.6 |
| | +GRA1 | 3.9 | 7.8 | 2.0 | 7.8 | 15.6 |
| | +GLY | 15.6 | 15.6 | 7.8 | 15.6 | 15.6 |
| | +JFB1 | 15.6 | 15.6 | 2.0 | 15.6 | 15.6 |
| | +JPE1 | 2.0 | 7.8 | 7.8 | 2.0 | 3.9 |
| | +LMB1 | 2.0 | 7.8 | 2.0 | 3.9 | 7.8 |

TABLE 5

MIC of Glycyrrhiza glabra Ethanol Extract Alone and in Combination With Antimicrobial Agent B

| Agent | | MIC (μg/ml) of Glycyrrhiza glabra Extract When Combined With Agent B for Identified Bacteria | | | | |
|---|---|---|---|---|---|---|
| A | B | AV | FN | PG | SM | SS |
| GLY | — | 15.0 | 15.6 | 12.1 | 15.6 | 6.6 |
| | +BX1 | 7.8 | 3.9 | 1.0 | 7.8 | 3.9 |
| | +RC1 | 3.9 | 2.0 | 2.0 | 3.9 | 3.9 |
| | +CR1 | 1.0 | 1.0 | 1.0 | 3.9 | 2.0 |
| | +TB1 | 1.0 | 1.0 | 7.8 | 15.6 | 1.0 |
| | +GRA1 | 3.9 | 3.9 | 3.9 | 3.9 | 1.0 |
| | +JFB1 | 1.0 | 2.0 | 2.0 | 1.0 | 2.0 |
| | +JPE1 | 3.9 | 2.0 | 3.9 | 1.0 | 1.0 |
| | +LMB1 | 3.9 | 3.9 | 2.0 | 3.9 | 1.0 |

TABLE 6

MIC of Geraniol Alone and in Combination With Antimicrobial Agent B

| Agent | | MIC (μg/ml) of Geraniol When Combined With Agent B for Identified Bacteria | | | | |
|---|---|---|---|---|---|---|
| A | B | AV | FN | PG | SM | SS |
| GRA1 | — | 133.3 | 82.3 | 147.9 | 133.3 | 127.1 |
| | +BX1 | 31.3 | 31.3 | 31.3 | 31.3 | 31.3 |
| | +RC1 | 62.5 | 15.6 | 15.6 | 31.3 | 31.3 |
| | +CR1 | 62.5 | 31.3 | 31.3 | 62.5 | 31.3 |

TABLE 6-continued

MIC of Geraniol Alone and in Combination With Antimicrobial Agent B

| Agent | | MIC (μg/ml) of Geraniol When Combined With Agent B for Identified Bacteria | | | | |
|---|---|---|---|---|---|---|
| A | B | AV | FN | PG | SM | SS |
| | +TB1 | 12.5 | 31.3 | 31.3 | 125 | 62.5 |
| | +GLY | 62.5 | 15.6 | 3.9 | 62.5 | 31.3 |
| | +JFB1 | 7.8 | 31.3 | 15.6 | 31.3 | 31.3 |
| | +JPE1 | 31.3 | 15.6 | 62.5 | 31.3 | 15.6 |
| | +LMB1 | 31.3 | 15.6 | 62.5 | 31.3 | 31.3 |

TABLE 7

MIC of Chloramphenicol Alone and in Combination With Antimicrobial Agent B

| Agent | | MIC (μg/ml) of Chloramphenicol When Combined With Agent B for Identified Bacteria | | | | |
|---|---|---|---|---|---|---|
| A | B | AV | FN | PG | SM | SS |
| CR1 | — | 5.4 | 1.8 | 6.9 | 5.2 | 3.2 |
| | +BX1 | 3.1 | 0.2 | 0.2 | 3.1 | 3.1 |
| | +RC1 | 0.4 | 1.6 | 0.8 | 3.1 | 0.8 |
| | +TB1 | 1.6 | 0.4 | 1.6 | 3.1 | 0.8 |
| | +GRA1 | 0.4 | 0.2 | 0.2 | 0.8 | 0.4 |
| | +GLY | 3.1 | 0.8 | 0.4 | 1.6 | 0.8 |
| | +JFB1 | 0.2 | 0.4 | 1.6 | 3.1 | 0.4 |
| | +JPE1 | 1.6 | 0.2 | 1.6 | 0.2 | 0.2 |
| | +LMB1 | 1.6 | 0.4 | 0.4 | 3.1 | 0.2 |

TABLE 8

MIC of Juicy Fruit Basil Oil Alone and in Combination With Antimicrobial Agent B

| Agent | | MIC (μg/ml) of Juicy Fruit Basil Oil When Combined With Agent B for Identified Bacteria | | | | |
|---|---|---|---|---|---|---|
| A | B | AV | FN | PG | SM | SS |
| JFB1 | — | 89.6 | 73.7 | 36.9 | 95.8 | 93.8 |
| | +BX1 | 62.5 | 31.3 | 3.9 | 31.3 | 15.6 |
| | +RC1 | 62.5 | 31.3 | 3.9 | 62.5 | 31.3 |
| | +CR1 | 31.3 | 3.9 | 3.9 | 3.9 | 31.3 |
| | +TB1 | 31.3 | 31.3 | 15.6 | 62.5 | 62.5 |
| | +GRA1 | 31.3 | 15.6 | 15.6 | 15.6 | 31.3 |
| | +GLY | 62.5 | 31.3 | 15.6 | 62.5 | 31.3 |
| | +JPE1 | 15.6 | 3.9 | 3.9 | 7.8 | 15.6 |
| | +LMB1 | 15.6 | 3.9 | 7.8 | 31.3 | 15.6 |

TABLE 9

MIC of Juniper Berries Oil Alone and in Combination With Antimicrobial Agent B

| Agent | | MIC (μg/ml) of Juniper Berries Oil When Combined With Agent B for Identified Bacteria | | | | |
|---|---|---|---|---|---|---|
| A | B | AV | FN | PG | SM | SS |
| JPE1 | — | 135.4 | 76.9 | 231.8 | 119.8 | 119.3 |
| | +BX1 | 31.3 | 31.3 | 7.8 | 62.5 | 31.3 |
| | +RC1 | 62.5 | 15.6 | 3.9 | 31.3 | 31.3 |
| | +CR1 | 31.3 | 7.8 | 15.6 | 62.5 | 31.3 |
| | +TB1 | 125 | 31.3 | 15.6 | 62.5 | 62.5 |
| | +GRA1 | 31.3 | 15.6 | 31.3 | 31.3 | 31.3 |
| | +GLY | 62.5 | 31.3 | 62.5 | 62.5 | 31.3 |
| | +JFB1 | 31.3 | 15.6 | 62.5 | 31.3 | 31.3 |
| | +LMB1 | 31.3 | 15.6 | 62.5 | 31.3 | 31.3 |

TABLE 10

MIC of Lemon Basil Oil Alone and in Combination With Antimicrobial Agent B

| Agent | | MIC (μg/ml) of Lemon Basil Oil When Combined With Agent B for Identified Bacteria | | | | |
|---|---|---|---|---|---|---|
| A | B | AV | FN | PG | SM | SS |
| LMB1 | — | 125 | 81.7 | 200.5 | 130.2 | 132.8 |
| | +BX1 | 31.3 | 15.6 | 7.8 | 31.3 | 15.6 |
| | +RC1 | 62.5 | 31.3 | 3.9 | 15.6 | 31.3 |
| | +CR1 | 31.3 | 15.6 | 31.3 | 7.8 | 62.5 |
| | +TB1 | 62.5 | 15.6 | 15.6 | 62.5 | 31.3 |
| | +GRA1 | 15.6 | 15.6 | 31.3 | 31.3 | 15.6 |
| | +GLY | 31.3 | 15.6 | 31.3 | 62.5 | 15.6 |
| | +JFB1 | 31.3 | 15.6 | 15.6 | 31.3 | 31.3 |
| | +JPE1 | 31.3 | 15.6 | 62.5 | 31.3 | 15.6 |

TABLE 11

MIC of Cocamidopropyl Dimethylglycine Alone and in Combination With Antimicrobial Agent B

| Agent | | MIC (μg/ml) of Cocamidopropyl Dimethylglycine When Combined With Agent B for Identified Bacteria | | | | |
|---|---|---|---|---|---|---|
| A | B | AV | FN | PG | SM | SS |
| TB1 | — | 28.9 | 45.4 | 16.8 | 22.8 | 30.2 |
| | +BX1 | 1.0 | 1.0 | 7.8 | 1.0 | 15.6 |
| | +RC1 | 1.0 | 7.8 | 2.0 | 1.0 | 0.1 |
| | +CR1 | 31.3 | 31.3 | 3.9 | 15.6 | 31.3 |
| | +GRA1 | 1.0 | 15.6 | 2.0 | 1.0 | 7.8 |
| | +GLY | 15.6 | 62.5 | 3.9 | 1.0 | 31.3 |
| | +JFB1 | 7.8 | 1.0 | 1.0 | 3.9 | 1.0 |
| | +JPE1 | 1.0 | 1.0 | 2.0 | 1.0 | 1.0 |
| | +LMB1 | 3.9 | 1.0 | 3.9 | 1.0 | 1.0 |

This example illustrates the effect that the addition of an antimicrobial agent B to antimicrobial agent A has on the MIC of antimicrobial agent A. The resulting data illustrate how the MIC of agent A when combined with agent B is reduced relative to the MIC of agent A alone.

EXAMPLE 2

Determination of MIC of Individual Agents and Three Antimicrobial Agents in Combination This example illustrates how combinations of three antimicrobial agents useful in gum compositions of the present invention inhibit visible in vitro growth of oral microorganisms. In addition, the example describes how the MIC of antimicrobial agents in the combinations are reduced compared to the MIC of those antimicrobial agents alone and the MIC of those agents in various pairings. Numerous combinations of the antimicrobial agents described herein were combined to form combinations comprising three antimicrobial agents or triplets. Each of the formed triplets included either cedarwood oil or berberine hydrochloride.

The protocol used was a variation of the procedure described above in Example 1. The assay was carried out in the two-dimensional array of a 96-well plate. In order to evaluate three agents, two of the agents were paired against the third agent. For example, varying concentrations of antimicrobial agent A plus antimicrobial agent B versus varying concentrations of antimicrobial agent C were evaluated on one 96-well plate. The procedure was repeated with the other two possible pairings, i.e., A+C with B, and B+C with A. Accordingly, each triplet required three assays in order to assess each of the three possible pairings.

The bacterial innoculum was prepared as described in Example 1.

A sterile polystyrene 96-well plate was used to dilute the antimicrobial agents A, B and C. Using aseptic technique, 100 microliters of distilled water was placed in each test well. The dilution scheme was separated into two parts. First, the dilution of the combined agents A and B and then second, the dilution of agent C. A dilution of agents A and B was accomplished by placing 50 microliters of stock solution for agent A in the first well of each column. Next, 50 microliters of stock solution for agent B was added to each of the first wells of each column. Accordingly, the first well of each column included 50 microliters of stock solution for agent A and 50 microliters of stock solution for agent B. 100 microliters from the first row in each column was then transferred to the next well in the column and so on down the column. Each transfer was a one-half dilution of the preceding concentration.

The dilution of antimicrobial agent C was accomplished by adding 100 microliters of agent C stock solution to the first well of each row. 100 microliters from the first well in each row was then transferred to the next well and so on across the row of test wells. Each transfer was a one-half dilution of the preceding concentration. FIG. 1 is a schematic illustration of the concentrations of antimicrobial agents A, B and C derived from the dilution scheme described above. The stock solution for each antimicrobial agent had an initial concentration of 2,500 micrograms per milliliter. As illustrated in FIG. 1, the concentration of agents A and B decreases down a given column. The concentration of agent C decreases across a row from left to right. Upon completion of the dilution of agent C, at least one column remained which included diluted stock solution of A and B, with any agent C. This column of wells was used to assess the MIC for agent A and agent B in combination. In addition, stock solution of agent C was diluted down one column which provided an indication of the MIC for agent C alone. 80 microliters of growth media specific for the bacteria under study was added to each well. The growth media specific for the bacteria are set forth above in Table 1.

Next, 20 microliters of innoculum was added to each well. This resulted in the first well having a final dilution one-eighth of the stock solutions for agent A and agent B, and one-quarter dilution of the stock solution for agent C. The remaining wells were a half-dilution of the preceding well for each transfer.

The 96-well plate was then incubated under conditions that varied by microorganism. Table 1 lists the microorganisms and the specific incubation conditions. In addition to the bacteria set forth in Table 1, the bacteria *Campylobacter rectus* (CR) was utilized. The growth media for *Campylobacter rectus* was 0.74% wt. to vol. brain heart infusion broth, 0.01% yeast extract, 0.2% sodium formate, 0.03% sodium fumerate, and 0.005% hemin, and 990 milliliters distilled water. The incubation conditions for *Campylobacter rectus* were 48 hours at 37° C. under anaerobic conditions. The plate was then read for microbial growth with a spectrophotometer by optical density. The well containing the lowest dilution achievable for each agent with a spectrophotometer reading below 0.05 OD was considered representative for the combination. The MIC for each agent was then determined by accounting for the starting stock solution concentration and the resulting dilutions in the 96 well plate.

The resulting data are summarized in Tables 12–15.

TABLE 12

MIC of Cedarwood Oil, Berberine Hydrochloride and Geraniol Alone, in Pairs, and in Combination

| Individual Agents Alone[1] | | | MIC (μg/ml) for Identified Bacteria | | | | |
|---|---|---|---|---|---|---|---|
| A | B | C | AV | FN | PG | SM | SS |
| RC1 | — | — | 31.3 | 62.5 | 15.6 | 31.3 | 7.8 |
| — | BX1 | — | 31.3 | 62.5 | 15.6 | 31.3 | 31.3 |
| — | — | GRA1 | 125 | 62.5 | 62.5 | 125 | 125 |
| Pairings of Agents A, B & C[2] | | | | | | | |
| RC1 | | | 15.6 | 15.6 | 7.8 | 15.6 | 3.9 |
| +BX1 | | | 15.6 | 15.6 | 7.8 | 15.6 | 3.9 |
| RC1 | | | 15.6 | 15.6 | 7.8 | 15.6 | 7.8 |
| +GRA1 | | | 31.3 | 31.3 | 15.6 | 31.3 | 15.6 |
| BX1 | | | 31.3 | 31.3 | 15.6 | 15.6 | 31.3 |
| +GRA1 | | | 62.5 | 31.3 | 31.3 | 31.3 | 62.5 |
| Triplets of Agents A, B & C[3] | | | | | | | |
| RC1 | | | 7.8 | 15.6 | 3.9 | 7.8 | 3.9 |
| | +BX1 | | 3.9 | 7.8 | 3.9 | 2.0 | 3.9 |
| | +GRA1 | | 7.8 | 7.8 | 7.8 | 3.9 | 7.8 |
| | BX1 | | 3.9 | 7.8 | 7.8 | 7.8 | 7.8 |
| | +RC1 | | 7.8 | 3.9 | 1.0 | 7.8 | 3.9 |
| | +GRA1 | | 15.6 | 7.8 | 2.0 | 15.6 | 7.8 |
| | GRA1 | | 7.8 | 15.6 | 15.6 | 31.3 | 31.3 |
| | +RC1 | | 7.8 | 3.9 | 1.0 | 7.8 | 1.0 |
| | +BX1 | | 7.8 | 3.9 | 1.0 | 7.8 | 1.0 |

[1]Directly to the right is shown the MIC values for each agent when used alone.
[2]Directly to the right is shown the MIC values for each agent in the presence of a second agent.
[3]Directly to the right is shown the MIC values for each agent in the presence of two additional agents.

TABLE 13

MIC of Cedarwood Oil, Berberine Hydrochloride and Juicy Fruit Basil Oil Alone, in Pairs, and in Combination

| Individual Agents Alone[1] | | | MIC (μg/ml) for Identified Bacteria | | | | |
|---|---|---|---|---|---|---|---|
| A | B | C | AV | FN | PG | SM | SS |
| RC1 | — | — | 15.6 | 31.3 | 62.5 | 15.6 | 15.6 |
| — | BX1 | — | 62.5 | 62.5 | 15.6 | 31.3 | 62.5 |
| — | — | JFB1 | 125 | 62.5 | 62.5 | 125 | 125 |
| Pairings of Agents A, B & C[2] | | | | | | | |
| RC1 | | | 15.6 | 15.6 | 7.8 | 15.6 | 7.8 |
| +BX1 | | | 15.6 | 15.6 | 7.8 | 15.6 | 7.8 |
| RC1 | | | 7.8 | 2.0 | 1.0 | 7.8 | 1.0 |
| +JFB1 | | | 15.6 | 31.3 | 2.0 | 15.6 | 2.0 |
| BX1 | | | 31.3 | 15.6 | 7.8 | 15.6 | 15.6 |
| +JFB1 | | | 62.5 | 31.3 | 15.6 | 31.3 | 31.3 |
| Triplets of Agents A, B & C[3] | | | | | | | |
| RC1 | | | 7.8 | 7.8 | 7.8 | 7.8 | 7.8 |
| | BX1 | | 15.6 | 3.9 | 2.0 | 7.8 | 3.9 |
| | +JFB1 | | 31.3 | 7.8 | 3.9 | 15.6 | 7.8 |

TABLE 13-continued

MIC of Cedarwood Oil, Berberine Hydrochloride and Juicy Fruit Basil Oil Alone, in Pairs, and in Combination

| Individual Agents Alone[1] | | | MIC (μg/ml) for Identified Bacteria | | | | |
|---|---|---|---|---|---|---|---|
| A | B | C | AV | FN | PG | SM | SS |
| BX1 | | | 15.6 | 15.6 | 3.9 | 7.8 | 31.3 |
| | RC1 | | 7.8 | 2.0 | 1.0 | 7.8 | 1.0 |
| | +JFB1 | | 15.6 | 3.9 | 2.0 | 15.6 | 2.0 |
| JFB1 | | | 62.5 | 15.6 | 15.6 | 62.5 | 62.5 |
| | +RC1 | | 1.0 | 2.0 | 2.0 | 1.0 | 2.0 |
| | +BX1 | | 1.0 | 3.9 | 2.0 | 1.0 | 2.0 |

TABLE 14

MIC of Cedarwood Oil, Geraniol and Juicy Fruit Basil Oil Alone, in Pairs, and in Combination

| Individual Agents Alone[1] | | | MIC (μg/ml) for Identified Bacteria | | | | |
|---|---|---|---|---|---|---|---|
| A | B | C | AV | FN | PG | SM | SS |
| RC1 | — | — | 31.3 | 31.3 | 7.8 | 31.3 | 31.3 |
| — | GRA1 | — | 62.5 | 62.5 | 62.5 | 125 | 62.5 |
| — | — | JFB1 | 125 | 62.5 | 15.6 | 125 | 62.5 |
| Pairings of Agents A, B & C[2] | | | | | | | |
| RC1 | | | 15.6 | 15.6 | 7.8 | 15.6 | 15.6 |
| +GRA1 | | | 31.3 | 31.3 | 15.6 | 31.3 | 31.3 |
| RC1 | | | 15.6 | 15.6 | 3.9 | 7.8 | 7.8 |
| +JFB1 | | | 31.3 | 31.3 | 7.8 | 15.6 | 15.6 |
| GRA1 | | | 31.3 | 31.3 | 15.6 | 62.5 | 31.3 |
| +JFB1 | | | 31.3 | 31.3 | 15.6 | 62.5 | 31.3 |
| Triplets of Agents A, B & C[3] | | | | | | | |
| RC1 | | | 15.6 | 15.6 | 3.9 | 3.9 | 7.8 |
| | +GRA1 | | 2 | 2 | 3.9 | 31.3 | 7.8 |
| | +JFB1 | | 2 | 2 | 3.9 | 31.3 | 7.8 |
| GRA1 | | | 15.6 | 31.3 | 15.6 | 31.3 | 15.6 |
| | +RC1 | | 3.9 | 2 | 1 | 2 | 2 |
| | +JFB1 | | 7.8 | 3.9 | 2 | 3.9 | 3.9 |
| JFB1 | | | 62.5 | 15.6 | 7.8 | 62.5 | 15.6 |
| | +RC1 | | 1 | 3.9 | 1 | 3.9 | 3.9 |
| | +GRA1 | | 2 | 7.8 | 2 | 7.8 | 7.8 |

TABLE 15

MIC of Berberine Hydrochloride, Juicy Fruit Basil Oil and Geraniol Alone, in Pairs, and in Combination

| Individual Agents Alone[1] | | | MIC (μg/ml) for Identified Bacteria | | | | |
|---|---|---|---|---|---|---|---|
| A | B | C | AV | FN | CR | SM | SS |
| BX1 | — | — | 62.5 | 62.5 | 125 | 62.5 | 62.5 |
| — | JFB1 | — | 125 | 125 | 250 | 125 | 125 |
| — | — | GRA1 | 125 | 125 | 250 | 125 | 250 |
| Pairings of Agents A, B & C[2] | | | | | | | |
| BX1 | | | 31.3 | 15.6 | 62.5 | 31.3 | 31.3 |
| +JFB1 | | | 62.5 | 31.3 | 125 | 62.5 | 62.5 |
| BX1 | | | 31.3 | 15.6 | 62.5 | 31.3 | 31.3 |
| +GRA1 | | | 62.5 | 31.3 | 125 | 62.5 | 62.5 |
| JFB1 | | | 62.5 | 31.3 | 125 | 62.5 | 62.5 |
| +GRA1 | | | 62.5 | 31.3 | 125 | 62.5 | 62.5 |
| Triplets of Agents A, B & C[3] | | | | | | | |
| BX1 | | | 15.6 | 15.6 | 62.5 | 15.6 | 15.6 |
| | +JFB1 | | 15.6 | 2 | 2 | 15.6 | 15.6 |
| | +GRA1 | | 15.6 | 2 | 2 | 15.6 | 15.6 |
| JFB1 | | | 31.3 | 31.3 | 31.3 | 31.3 | 31.3 |
| | +BX1 | | 7.8 | 2 | 31.3 | 7.8 | 7.8 |
| | +GRA1 | | 15.6 | 3.9 | 62.5 | 15.6 | 15.6 |

TABLE 15-continued

MIC of Berberine Hydrochloride, Juicy Fruit Basil Oil and Geranoil Alone, in Pairs, and in Combination

| Individual Agents Alone[1] | | | MIC (μg/ml) for Identified Bacteria | | | | |
|---|---|---|---|---|---|---|---|
| A | B | C | AV | FN | CR | SM | SS |
| GRA1 | | | 31.3 | 31.3 | 31.3 | 31.3 | 31.3 |
| | +BX1 | | 7.8 | 1 | 15.6 | 7.8 | 7.8 |
| | +JFB1 | | 15.6 | 2 | 31.3 | 15.6 | 15.6 |

This example illustrates how the MIC of certain antimicrobial agents A, B and C in combination is reduced relative to the MIC of the individual antimicrobial agents in the absence of the other antimicrobial agents.

EXAMPLE 3

Ethanol Extraction of *Glycyrrhiza glabra*

25 grams of powdered plant material from *Glycyrrhiza glabra* was combined with 250 grams of a 95:5 ethanol/water mixture. The mixture was stirred overnight at room temperature. Solids were removed from the stirred mixture with a No. 4 Whatman filter in a Buchner funnel. Further removal of solids was achieved with a No. 5 Whatman filter in a Buchner funnel. Additional solids were removed with a Whatman 1 micrometer filter in a Buchner funnel. A vacuum filtration apparatus and a 0.2 micrometer filter was employed to clean the solution a final time. The clean solution was then concentrated down to a solid using a rotovaporizer. Approximately, 2.5 grams of a rust colored solid was collected as the crude extract of *Glycyrrhiza glabra*.

The following examples illustrate the effectiveness of individual antimicrobial agents useful in gum compositions formed in accordance with the present invention against bacteria present in the oral cavity, the MIC for the antimicrobial agents in the compositions against such bacteria, and gum formulations including antimicrobial agents in accordance with the present invention.

EXAMPLE 4

Determination of Minimum Inhibitory Concentration of Antimicrobial Agents

The following example illustrates how antimicrobial agents useful in gum compositions of the present invention retard or prevent the growth of dental plaque bacteria present in the oral cavity. In addition, the example illustrates the lowest concentration of various antimicrobial agents that will inhibit visible in vitro growth of a particular bacteria.

The assay used a microtiter plate to dilute the antimicrobial agent to varying concentrations in order to determine the MIC.

Table 16 below provides a listing of antimicrobial agents used in this example and abbreviations therefor.

TABLE 16

Antimicrobial Agents and Abbreviations Therefor

| | |
|---|---|
| cedarwood oil | (RC1) |
| chloramphenicol | (CR1) |
| *Glycyrrhiza glabra* ethanol extract | (GLY) |
| juicy fruit basil oil | (JFB1) |
| lemon basil oil | (LMB1) |

A bacteria culture was incubated overnight at 37° C. Prior to dilution of the antimicrobial agents as described below, the bacterial culture was spun down at 2000 rpm into a pellet and resuspended in a solution of buffered phosphate. The innoculum was normalized with a spectraphotometer to an optical density at 550 nanometers of between 0.18–0.22, equivalent to $5.0 \times 10^7$ colony-forming units (CFU per milliliter). The innoculum was set aside until the completion of the antimicrobial agent dilution.

A sterile polystyrene 96-well plate was used to dilute the antimicrobial agents. Using aseptic technique, 100 microliters of distilled water was placed in each test well. In the first well in each column, 100 microliters of antimicrobial agent was added. Stock solutions of antimicrobial agents were prepared with methanol as a solvent to bring the agents into solution. This resulted in a one-half dilution of the stock solution. 100 microliters from these wells was then transferred to the next well in the column, and so on, down each column. Each transfer accomplished a one-half dilution of the concentration in the preceding well. After the dilution of the antimicrobial agent was completed, 80 microliters of growth media specific for the bacteria under study was added to each well. The specific growth media for a given bacteria are set forth in Table 17.

Next, 20 microliters of innoculum was added to each well. This resulted in the first well of each column having a final dilution of one quarter of the stock solution. The remaining wells were a one-half dilution of the preceding well for each transfer.

The 96-well plate was incubated under conditions that varied depending on the particular microorganism. The incubation conditions are set forth in Table 17. The aerobic bacteria were incubated under normal room conditions and the anaerobic bacteria were incubated under an atmosphere of 10% hydrogen gas, 5% carbon dioxide gas and the balance nitrogen gas. Following 48 hours of incubation, the incubated plate was read for microbial growth with a spectraphotometer by optical density (OD). The well containing the lowest dilution achievable with a spectraphotometer reading below 0.05 OD (i.e., no detectable microbial growth) was considered representative for the antimicrobial agent. The MIC for the agent was determined by accounting for the starting stock solution concentration and the resulting dilutions in the 96-well plate.

The specific bacteria inoculated into the 96-well plate are set forth in Table 17 below, along with the growth media and incubation conditions for that microorganism.

TABLE 17

Microorganisms/Growth Media/Incubation Conditions

| Microorganism | ATCC No. | Growth Media | Incubation Conditions |
|---|---|---|---|
| *Campylobacter rectus* (CR) | 33238 | CR media[4] | 48 hrs/37° C./anaerobic |
| *Actinomyces viscosus* (AV) | 19246 | TSB[1] | 48 hrs/37° C./aerobic |
| *Fusobacterium nucleatum* (FN) | 10933 | FN media[3] | 48 hrs/37° C./anaerobic |
| *Porphyromonas gingivalis* (PG) | 33277 | PG media[2] | 48 hrs/37° C./anaerobic |
| *Streptococcus mutans* (SM) | 25175 | TSB[1] | 48 hrs/37° C./aerobic |
| *Streptococcus sanguis* (SS) | 49295 | TSB[1] | 48 hrs/37° C./aerobic |

[1]Tryptic Soy Broth 3.0% wt. to vol., yeast extract 0.1%, and 999 milliliters distilled water.
[2]Tryptic Soy Broth 3.0% wt. to vol., yeast extract 0.5%, L-cystein 0.05%, Hemin 0.0005%, Menadione 0.00002%, and 990 milliliters distilled water.
[3]Tryptic Soy Broth 3.0% wt. to vol., yeast extract 0.5%, Peptone 1.0%, L-cystein extract, Hemin 0.0005%, Menadione 0.00002%, and 990 milliliters distilled water.
[4]Brain Heart Infusion Broth 0.74% wt. to vol., yeast extract 0.01%, sodium formate 0.2%, sodium fumerate 0.03%, hemin 0.005% and 990 milliliters distilled water.

In the following tables, the antimicrobial agents are identified with respect to the abbreviations set forth in Table 16. In addition, the five microorganisms set forth in Table 17 are referred to by the abbreviations set forth in Table 17.

TABLE 18

MIC (µg/ml) for Antimicrobial Agents for Indicated Bacteria

| Agent | AV | CR | FN | PG | SM | SS |
|---|---|---|---|---|---|---|
| RC1 | 31.3 | 31.3 | 31.3 | 7.8 | 31.3 | 15.6 |
| CR1 | 3.1 | — | 3.1 | 6.3 | 3.1 | 3.1 |
| GLY | 15.6 | 15.6 | 15.6 | 7.8 | 15.6 | 7.8 |
| JFB1 | 156.3 | 156.3 | 156.3 | 62.5 | 156.3 | 156.3 |
| LMB1 | 125 | 125 | 62.5 | 31.3 | 62.5 | 62.5 |

This example illustrates the minimum inhibitory concentration of the individual noted antimicrobial agents and the ability of the individual antimicrobial agents to inhibit growth of the specific bacteria.

EXAMPLE 5

Gum Formulations

Six chewing gum formulations containing six different antimicrobial agents as described below were formed by incorporating the agents into a peppermint gum base formulation provided by the W. Wrigley Company. Ten volunteers chewed 2.7 grams samples of each gum formulation and provided saliva samples at intervals and the gum bolus at the end of the 25 minute chewing period. High pressure liquid chromatography and gas chromatography were used to analyze the gum bolus and saliva non-volatile and volatile components, respectively. The following Table 19 provides the percent of the particular antimicrobial agents that were released from the gum bolus after 25 minutes and provides an indication of whether or not the concentration in the saliva at any time was above the MIC for the particular agent.

TABLE 19

Release Properties

| Ingredient | Release from Chewed Gum Bolus after 25 min | Above MIC in Saliva (Y/N) |
| --- | --- | --- |
| Glycyrrhizic Acid, ammonium salt (GR) | 85% | Yes |
| G. glabra extract (GLY) | 65% | Yes |
| Menthol (from Peppermint flavoring)[1] | 50% | No |
| Rosemary Oil (ROF1)[1] | 38% | Not Determined |
| Cedarwood Oil (RC1) | 38% | Yes |
| Geraniol (GRA1) | 34% | No |
| Glycerrhetinic Acid (GA)[1] | 15% | No |

[1]Comparative example. Not an illustration of the present invention.

The active ingredients that were employed are set forth below in Table 40.

TABLE 20

Antimicrobial Agents

| Ingredient | Source |
| --- | --- |
| G. glabra extract (GLY) 2.74% glabridin by weight | Optiva |
| Cedarwood Oil (RC1) | Spectrum |
| Geraniol (GRA) | Lebermuth |
| Glycyrrhizic Acid, Monoammonium salt (GR) | Acros |
| 18β-Glycyrrhetinic acid (GA) | Acros |

The MIC Range was determined against a standard panel of five organisms that included *Actinomyces viscosus, Fusobacterium nucleatum, Porphyromonas gingivalis, Streptococcus mutans,* and *Stretococcus sanguis.* The starting dilution was 0.1 percent in methanol. The MIC used in this Example 5 was the MIC for each agent relative to *Porphyromonas gingivalis.* The MICs were as follows:

RC1→2.9; GLY→2.0; GRA→7.8; and menthol→125.

Table 21 below indicates the concentration of the various active agents that were incorporated into the gum base as a weight percent.

TABLE 21

| Gum Formulation | GLY | RC1 | GRA | ROF1 | GR | GA |
| --- | --- | --- | --- | --- | --- | --- |
| 1 | 0.5 | — | — | — | — | — |
| 2 | — | 1.0 | — | — | — | — |
| 3 | 0.5 | 1.0 | — | — | — | — |
| 4 | 0.5 | 1.0 | 0.05 | — | — | — |
| 5 | 0.5 | 1.0 | 0.05 | 0.25 | — | — |
| 6 | 0.5 | 1.0 | 0.05 | — | 0.25 | 0.25 |

Saliva samples were collected from each of the individuals prior to chewing 2.7 grams of gum, and at 1.0, 2.5, 5.0, 10.0, and 25.0 minutes while chewing the gum. The saliva samples were refrigerated until analysis. The gum bolus that remained after 25 minutes was saved and extracted immediately or stored refrigerated until extraction for analysis.

Analysis Method for GLY, GR and GA in Gum

To either 2.7 grams unchewed gum sample or the remaining bolus of chewed gum, was added 3.0 milliliters of internal standard (Hesperetin) in methanol, 6.0 milliliters hexane and 3.0 milliliters distilled water. Samples were homogenized using a Polytron Homogenizer model PT10/35 from Brinkmann Instruments, fitted with a PTA10TS generator for at least 30 seconds on ice, or until no lumps of non-dispersed gum were visible in the sample. Samples were then centrifuged in a Dynac Tabletop Centrifuge at top speed for ten minutes. The lower, amber, aqueous/methanol layer were then filtered through 25 millimeter, 0.45 micrometer nylon Acrodisc syringe filters from Gelman into 4 milliliter autosampler vials and tightly capped with polytetrafluorothylene lined septum in open-top screw caps. These samples were then analyzed using high pressure liquid chromatography for glabridin and/or glycyrrhizic and 18β-glycyrrhetinic acid, and were quantitated against a 4-point linear curve prepared by spiking approximately 2.7 grams unchewed samples of Wrigley Extra Sugarfree Peppermint gum with known levels of purified glabridin, glycyrrhizic acid monoammonium salt and 18β-glycyrrhetinic acid. Both the "blank" gums spiked with known levels of active agents and analyzed as unknowns and "blank" gum controls were prepared and analyzed using this same procedure to demonstrate the absence of interfering peaks from other gum constituents, and the accuracy of the analytical results.

Analysis Method for GLY, GR and GA in Saliva

To 500 μL saliva was added 700 μL acetonitrile or methanol (methanol was found to be necessary for the 1-minute saliva samples due to components from the gum causing acetonitrile to be immiscible with the aqueous portion). Samples were Vortex-mixed in Multi-tube vortex mixer for one minute and then centrifuged at top speed in clinical centrifuge for two minutes. Supernatants were carefully transferred to 1 milliliter glass shell vials and capped. Analysis was carried out either by isocratic elution for glabridin-only samples, or gradient elution for the samples containing the glycyrrhizic and 18β-glycyrrhetinic acids using high pressure liquid chromatography. Glabridin concentrations were converted to GLY concentrations by taking the weight percent glabridin in GLY to be 2.74 percent. The results of the analysis for GLY, GR and GA in saliva are reported in Table 22 below.

The calibration curve was prepared using spiked blank saliva. Both positive and negative controls were prepared and analyzed using the same procedure to demonstrate the absence of the interfering peaks from other compounds, and the accuracy of the analytical results.

Analysis Methods for Essential Oils: Menthol, RC1, GRA, and ROF1 in Saliva and Gum Method 20 (GC Method for Flavorings and RC1 in Dentifrice) was modified as two separate methods for analysis of gum saliva and gum bolus, respectively.

For saliva, the essential oils of menthol, cedarwood oil, geraniol and *Rosmarinus officianalis* were determined by capillary gas chromatography. The split ratio was 25:1. The injection volume was 2 μL. Four hundred μL of saliva was extracted from the 1 milliliter of ethyl acetate containing an internal standard (hexadecane) in 1.5 milliliter Eppendorf tubes. After centrifugation, the organic layer was injected directly into the Hewlett-Packard 6890 gas chromatograph. Under the conditions employed, the only components that were not subject to interference from peppermint oil were, geraniol (from geraniol oil, 90%) and cedrene/thujopsene (from RC1). The principal components of ROF1 were not measurable since the peaks were overlapped with those of peppermint oil. Due to limitations of the flame ionization detector, RC1 was only observed in a few samples. For this reason, only the samples from 0 to 10 minutes were analyzed. A cleanup gradient was run from 190 to 300° C. every fifth sample to remove less volatile interferences from the column. The results of the analysis for menthol, RC1, GRA, and ROF1 in saliva are set forth below in Table 22. The concentration levels for RC1 at time intervals 2.5, 5.0, 10.0, and 25.0 were below detection limits. The same applies for the concentration for GRA and menthol at 25 minutes.

Figure 2:
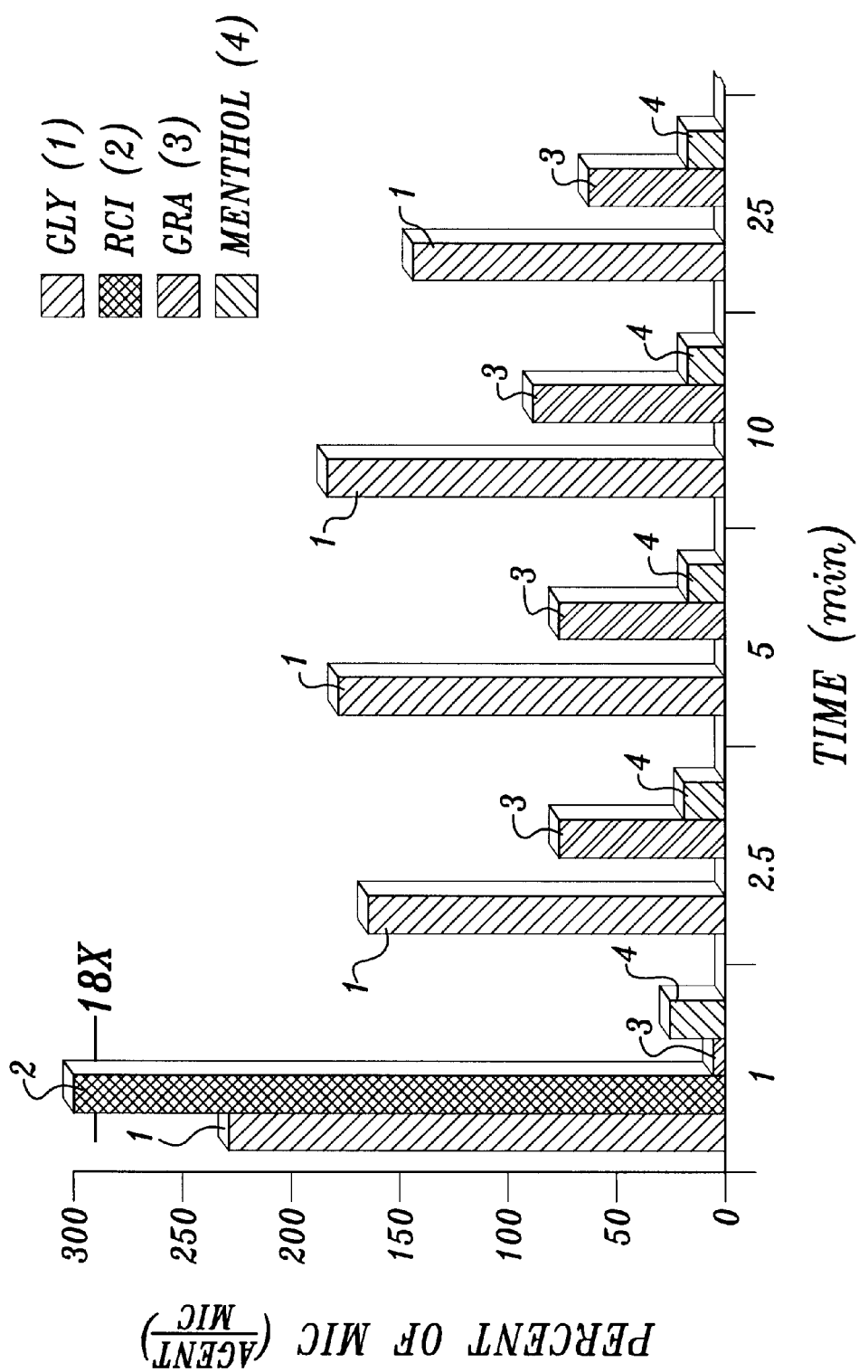
FIG. 2 is a bar chart illustrating the ratio of the concentration of an antimicrobial agent in saliva to the MIC of that agent (relative to *Porphyromonas gingivalis*) as a function of the length of time that a gum including such agent is chewed.

Using a MIC with respect to *Porphyromonas gingivalis* of 2.0 for GLY, 2.9 for RC1, 7.8 for GRA, and 125 for menthol, the bar chart illustrated in FIG. 2 was created. From that chart, it can be seen how RC1 is released quickly from the gum composition formed in accordance with the present invention while GLY and GRA are released more slowly and over a longer period of time in accordance with the present invention.

For the analysis of the gum bolus, both chewed and unchewed, a Polytron Homogenizer, described above was used. The gum sample was placed in a heavy wall glass tube. Internal standard (1 μL) ethyl acetate (5 μL) and water (4 μL) were added. The sample was homogenized for approximately 30 seconds, or until no particles could be seen. The tubes were then centrifuged for 10 minutes on a clinical centrifuge at maximum speed. The supernatant was injected directly onto the gas chromatograph. The oven program was modified to allow resolution of ROF1 components from those of the peppermint flavoring. The gas chromatograph was calibrated using a three point standard curve to quantify the following components: menthol (flavor); geraniol (oil geraniol); cedrene, thujopsene (RC1); pinene, cineol, camphor, bornyl acetate (ROF1). The initial temperature was decreased from 140° C. to 100° C. The temperature gradient was changed from 10° C./minute to 4° C./minute. The split ratio was 50:1, and injection volume was 1 μL as per the method. A cleanup gradient was run every fifth sample as described previously.

A recovery study was performed in triplicate using blank Wrigley's Peppermint Gum (chewed and unchewed) spiked with stand and solution. Recovery was calculated relative to a direct standard consisting of spike solution without sample matrix.

TABLE 22

Concentration (μg/ml) of Antimicrobial Agent in Saliva as a Function of Time

| Time (Minutes) | 1 | 2.5 | 5.0 | 10.0 | 25 |
|---|---|---|---|---|---|
| GLY[5] | 4.6 | 3.3 | 3.6 | 3.7 | 2.9 |
| RC1[4] | 69 | — | — | — | — |
| GRA[3] | 6 | 6 | 7 | 5 | — |
| GA[1,2] | 1.8 | 1.5 | 1.6 | 1.8 | 2.3 |
| GR[2] | 3105 | 111 | 55 | 30 | 10 |
| Menthol[1,6] | 25 | 22 | 24 | 24 | — |

[1]Comparative example. Not an illustration of the present invention.
[2]Based on gum formulation #6 only.
[3]Based on gum formulations 4–6.
[4]Based on gum formulations 5 and 6.
[5]Based on gum formulations 1, 3–6.
[6]Based on gum formulations 1–6.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A gum composition comprising:
  antimicrobial agent A and antimicrobial agent B in an amount effective to inhibit the growth of oral pathogenic bacteria selected from the group consisting of *Actinomyces viscosus, Fusobacterium nucleatum, Porphyromonas gingivalis, Streptococcus mutans,* and *Streptococcus sanguis,* antimicrobial agent A and antimicrobial agent B being selected from the group consisting of berberine, cedarwood oil, chloramphenicol, *Glycyrrhiza glabra* extract, juicy fruit basil oil, juniper berries oil, and lemon basil oil, wherein when antimicrobial agent A and antimicrobial agent B are combined at least one of antimicrobial agent A and antimicrobial agent B exhibit a minimum inhibitory concentration relative to at least one of the bacteria that is synergistically less than the minimum inhibitory concentration of the at least one antimicrobial agent alone.

2. The composition of claim 1, wherein at least one of the agents is selected from the group consisting of cedarwood oil, berberine, and *Glycyrrhiza glabra* extract.

3. The composition of claim 2, wherein at least one of the agents is cedarwood oil and the other agent is selected from the group consisting of berberine and *Glycyrrhiza glabra* extract.

4. The composition of claim 1, wherein one of the agents is *Glycyrrhiza glabra* extract and the other agent is selected from the group consisting of juicy fruit basil oil and juniper berries oil.

5. The composition of claim 1, wherein one agent is juicy fruit basil oil and the other agent juniper berries oil.

6. The composition of claim 1, wherein one agent is juniper berries oil and the other agent is lemon basil oil.

7. The composition of claim 1, wherein one agent is *Glycyrrhiza glabra* extract and the other agent is cedarwood oil.

8. A gum composition comprising:
  an antimicrobial agent A comprising geraniol; and
  an antimicrobial agent B selected from the group consisting of berberine, cedarwood oil, chloramphenicol, cocamidopropyl dimethylglycine, *Glycyrrhiza glabra* extract, juicy fruit basil oil, juniper berries oil and lemon basil oil, antimicrobial agent A and antimicrobial agent B being present in an amount effective to inhibit the growth of oral pathogenic bacteria selected from the group consisting of *Actinomyces viscosus, Fusobacterium nucleatum, Porphyromonas gingivalis, Streptococcus mutans,* and *Streptococcus sanguis,* wherein when antimicrobial agent A and antimicrobial agent B are combined at least one of antimicrobial agent A and antimicrobial agent B exhibits a minimum inhibitory concentration relative to at least one of the bacteria that is synergistically less than the minimum inhibitory concentration of the at least one antimicrobial agent alone.

9. A gum composition comprising:
  an antimicrobial agent A comprising cocamidopropyl dimethylglycine; and
  an antimicrobial agent B selected from the group consisting of berberine, cedarwood oil, chloramphenicol, *Glycyrrhiza glabra* extract, juicy fruit basil oil, juniper berries oil and lemon basil oil, antimicrobial agent A and antimicrobial agent B being present in an amount effective to inhibit the growth of oral pathogenic bacteria selected from the group consisting of *Actinomyces viscosus, Fusobacterium nucleatum, Porphyromonas gingivalis, Streptococcus mutans,* and *Streptococcus sanguis* and wherein when antimicrobial agent A and antimicrobial agent B are combined at least one of antimicrobial agent A and antimicrobial agent B exhibits a minimum inhibitory concentration relative to at least one of the bacteria that is synergistically less than the minimum inhibitory concentration of the at least one antimicrobial agent alone.

10. A gum composition comprising:
- a first antimicrobial agent that is released from a gum base to the oral cavity to provide a concentration in the oral cavity above the MIC of the first antimicrobial agent within about one to five minutes of initiation of gum chewing; and
- a second antimicrobial agent that is released from the gum base to the oral cavity to provide a concentration in the oral cavity above the MIC of the second antimicrobial agent after about five minutes from initiation of gum chewing.

11. The gum composition of claim 10 wherein the first antimicrobial agent is cedarwood oil and the second antimicrobial agent is selected from the group consisting of *Glycyrrhiza glabra* ethanol extract, geraniol and glycyrrhizic acid.

12. The gum composition of claim 11, wherein the second antimicrobial agent is selected from the group consisting of *Glycyrrihiza glabra* ethanol extract and geraniol.

13. The gum composition of claim 11, wherein the second antimicrobial agent is *Glycyrrihiza glabra* ethanol extract.

14. A method for inhibiting the growth of oral pathogenic bacteria in the oral cavity comprising:
- releasing cedarwood oil from a gum to the oral cavity to provide a concentration of cedarwood oil in the oral cavity above the minimum inhibitory concentration of cedarwood oil within about one to five minutes of initiation of gum chewing; and
- releasing at least one antimicrobial agent selected from the group consisting of *Glycyrrhiza glabra* extract, geraniol and glycyrrhizic acid from the gum to the oral cavity to provide a concentration of the at least one antimicrobial agent in the oral cavity above the minimum of the at least one antimicrobial agent after about five minutes from initiation of gum chewing.

15. The method of claim 14, wherein the at least one antimicrobial agent is selected from the group consisting of *Glycyrrihiza glabra* extract and geraniol.

16. The method of claim 15, wherein the at least one antimicrobial agent is *Glycyrrihiza glabra* ethanol extract.

17. A method of manufacturing a gum comprising:
incorporating cedarwood oil into a gum base; and
incorporating at least one antimicrobial agent selected from the group consisting of *Glycyrrihiza glabra* extract, geraniol and glycyrrhizic acid into the gum base.

18. The method of claim 17, wherein the at least one antimicrobial agent is selected from the group consisting of *Glycyrrihiza glabra* extract and geraniol.

19. The method of claim 18, wherein the at least one antimicrobial agent is *Glycyrrihiza glabra* ethanol extract.

* * * * *

UNITED STATES PATENT AND TRADEMARK OFFICE
CERTIFICATE OF CORRECTION

PATENT NO. : 6,248,309 B1
DATED : June 19, 2001
INVENTOR(S) : L.M. Iyer et al.

It is certified that error appears in the above-identified patent and that said Letters Patent is hereby corrected as shown below:

<u>Title page,</u>
Item [56], References Cited,
U.S. PATENT DOCUMENTS,
Item 27, "Sampathjkumar" should read-- Sampathkumar --

OTHER PUBLICATIONS,
Item 11, "componets";" should read -- components"; --
Item 11, "001890599;" should read -- 0018-0599; --

Signed and Sealed this

Twenty-sixth Day of February, 2002

Attest:

JAMES E. ROGAN
Attesting Officer
Director of the United States Patent and Trademark Office